(12) United States Patent
Bae et al.

(10) Patent No.: US 7,655,120 B2
(45) Date of Patent: Feb. 2, 2010

(54) BIOSENSOR

(75) Inventors: Byeong-woo Bae, Anyang-si (KR);
Sung-dong Lee, Yeongcheon-si (KR);
Hong-seong Suk, Anyang-si (KR); Jina Yoo, Anyang-si (KR); Min-sun Kim, Seoul (KR); Jae-hyun Yoo, Seoul (KR); Ki-won Lee, Seoul (KR)

(73) Assignee: Infopia Co., Ltd. (KR)

( * ) Notice: Subject to any disclaimer, the term of this patent is extended or adjusted under 35 U.S.C. 154(b) by 302 days.

(21) Appl. No.: 11/548,457

(22) Filed: Oct. 11, 2006

(65) Prior Publication Data

US 2008/0087543 A1    Apr. 17, 2008

(51) Int. Cl.
*G01N 27/327*    (2006.01)

(52) U.S. Cl. .............................. 204/403.14; 204/403.02

(58) Field of Classification Search ............... 204/403.01–403.15; 205/777.5, 778, 792
See application file for complete search history.

(56) References Cited

U.S. PATENT DOCUMENTS 5,437,999 A  *  8/1995  Diebold et al. ......... 204/403.11
5,876,952 A  *  3/1999  Shieh ....................... 435/14
6,156,173 A     12/2000  Gotoh et al.
6,299,757 B1 * 10/2001  Feldman et al. ............. 205/775
6,616,819 B1    9/2003  Liamos et al.

FOREIGN PATENT DOCUMENTS

| EP | 1067384 A2 | 1/2001 |
|---|---|---|
| EP | 1369686 A2 | 12/2003 |
| WO | WO0248707 | 6/2002 |
| WO | WO03056345 | 7/2003 |

OTHER PUBLICATIONS

European Office Action; 06020878.2-2204; Apr. 16, 2007. All references cited in the Office action and not previously submitted are listed above.

* cited by examiner

*Primary Examiner*—Alex Noguerola
(74) *Attorney, Agent, or Firm*—Cantor Colburn LLP

(57) ABSTRACT

A biosensor measuring an analyte contained in a sample is provided, including: an insulative lower substrate that has at least one electrode on which an enzyme reaction layer reacting with the analyte is formed; an upper substrate that faces the lower substrate and is made of a conductive material; and an adhesive layer that has a sample feed with a predetermined height on the enzyme reaction layer and attaches the upper and lower substrates to each other, where an end of the upper substrate acts as an electrode in which an electron-transfer mediator contained in the enzyme reaction layer is oxidized or reduced, and the other end acts as an electrical contact part that electrically contacts a measurement unit.

12 Claims, 7 Drawing Sheets

BIOSENSOR

BACKGROUND OF THE INVENTION

1. Field of the Invention

The present invention relates to a biosensor and, more particularly, to a biosensor that electrochemically detects an analyte contained in a bio-sample.

2. Discussion of the Background

It is important in clinical diagnosis that an analyte contained in a bio-sample should be analyzed in a quantitative or qualitative manner. For example, a blood glucose level is measured from a blood sample of a patient suffering from diabetes, or a cholesterol level is measured to check adult diseases. Patients suffering from diabetes should measure their blood glucose levels at regular intervals. A number of companies have been releasing products for blood glucose measurement into markets.

In general, most of the products for blood glucose measurement measure blood glucose levels of blood extracted from patients using biosensors. However, since it causes pain to a patient to extract blood from the patient, a minimum amount of blood should be extracted from the patient so that the patient feels the pain less.

According to U.S. Pat. Nos. 6,156,173, 6,616,819 and 5,437,999, it is configured such that electrodes face each other to extract a minimum amount of blood required for measurement. In a conventional biosensor, working electrode, reference electrode and/or counter electrode are formed on a single substrate. In the above-mentioned U.S. Patents, however, the electrodes are formed on upper and lower substrates to face each other, thus minimizing the amount of blood required for measurement.

However, in the above-mentioned U.S. Patents, additional electrodes should be formed on the upper and lower substrates made of insulating material so that the electrodes can face each other. In addition, the electrodes formed on the upper and lower substrates should be made of conductive material to be connected to each other. As a result, there is a problem in that the fabrication process becomes complicated and the production cost increases relative to the conventional method in which the electrodes are formed on a single substrate.

SUMMARY OF THE INVENTION

The present invention provides a biosensor that uses a least amount of blood and is manufactured by a simplified manufacture process.

Additional features of the invention will be set forth in the description which follows, and in part will be apparent from the description, or may be learned by practice of the invention.

The present invention discloses a biosensor measuring an analyte contained in a sample, including: an insulative lower substrate that has at least one electrode on which an enzyme reaction layer reacting with the analyte is formed; an upper substrate that faces the lower substrate and is made of a conductive material; and an adhesive layer that has a sample feed with a predetermined height on the enzyme reaction layer and attaches the upper and lower substrates to each other, where an end of the upper substrate acts as an electrode in which an electron-transfer mediator contained in the enzyme reaction layer is oxidized or reduced, and the other end acts as an electrical contact part that electrically contacts a measurement unit.

The one end of the upper substrate acting as an electrode may face the electrode formed on the lower substrate.

The present invention also discloses a biosensor measuring an analyte contained in a sample, including: an insulative lower substrate that has at least one electrode on which an enzyme reaction layer reacting with the analyte is formed; an upper substrate that faces the lower substrate and is made of a conductive material; and an adhesive layer that has a sample feed with a predetermined height on the enzyme reaction layer and attaches the upper and lower substrates to each other, where an electrode is formed on a lower side of an end of the upper substrate in which an electron-transfer mediator contained in the enzyme reaction layer is oxidized or reduced, and the other end acts as an electrical contact part that electrically contacts a measurement unit.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

The invention is described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. In the drawings, the size and relative sizes of layers and regions may be exaggerated for clarity. Like reference numerals in the drawings denote like elements.

It will be understood that when an element or layer is referred to as being "on" or "connected to" another element or layer, it can be directly on or directly connected to the other element or layer, or intervening elements or layers may be present. In contrast, when an element is referred to as being "directly on" or "directly connected to" another element or layer, there are no intervening elements or layers present.

Unlike the above-mentioned conventional methods in which an upper substrate is made of an insulating material and an additional electrode is formed on the upper substrate, the present invention features that since the upper substrate is made of a conductive material and is used as an electrode, no additional electrode is needed and the fabrication process is simple. That is, the upper substrate is made of a conductive material such that an electron-transfer mediator generated by reacting with an analyte contained in a sample is easily oxidized or reduced.

In general, a biosensor is a device for the detection of an analyte that combines a biological component with a physicochemical detector component. It includes a working electrode, and a reference electrode and/or a counter electrode. For example, an electrochemical sensor makes a measurement using oxidoreductase and electron-transfer mediator according to the following reaction formula.

[Reaction Formula]

analyte+enzyme (oxidized)+electron-transfer mediator (oxidized)→resultant substance+enzyme (oxidized)+electron-transfer mediator (reduced)

In the above-mentioned reaction formula, the reduced electron-transfer mediator is proportional to the concentration of an analyte contained in a sample. In this case, the reduced electron-transfer mediator is oxidized by applying a predetermined voltage to a working electrode with respect to a reference or counter electrode. At this time, by measuring the amount of oxidation current, it is possible to make a quantitative analysis of the analyte contained in the sample.

Examples of the enzyme include oxidoreductase, such as glucose oxidase, lactate oxidase, cholesterol oxidase, or alcohol oxidase, transferase, such as glutamate oxaloacetate transaminase (GOT) or glutamate pyruvate transaminase (GPT), or hydrolase.

Examples of the electron-transfer mediator include potassium ferricyanide, potassium ferrocyanide, hexaamineruthenium chloride, ferrocene and its derivatives, or quinine and its derivatives.

The material which makes up the working electrode is composed of carbon, graphite, platinum-plated carbon, silver, gold, palladium, or platinum. For example, ink composed of carbon or platinum-plated carbon, or ink containing palladium may be used to print the working electrode on a lower substrate. The working electrode may be formed on the lower electrode by a vacuum deposition method using gold.

The biosensor will be described in detail.

Figure 1A:
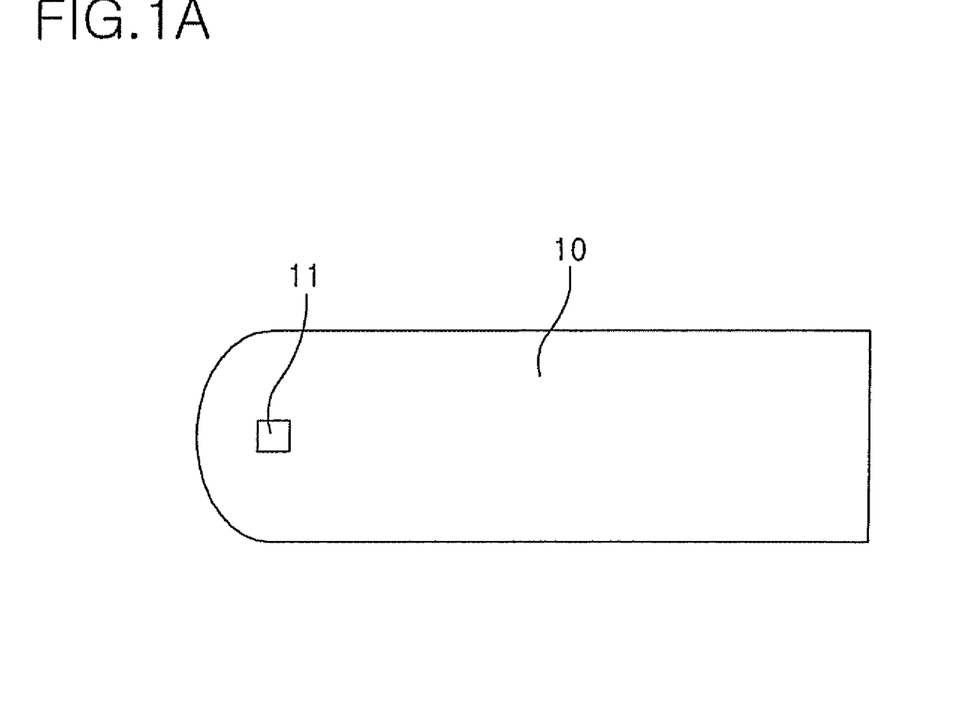
FIG. 1A shows a plan view of an upper substrate of a biosensor according to an exemplary embodiment of the present invention.

FIG. 1A shows a plan view of an upper substrate of a biosensor according to an exemplary embodiment of the present invention.

An air outlet 11 is formed on an upper substrate 10 so that a sample can be injected through capillary action. The upper substrate 10 is made of conductive material such that an oxidized or reduced electron-transfer mediator generated by reaction with an analyte contained in the sample is easily oxidized or reduced. Accordingly, since the material that makes up the upper substrate is used as an electrode, an additional electrode is not required and the fabrication process of the sensor is thus simplified.

Figure 1B:
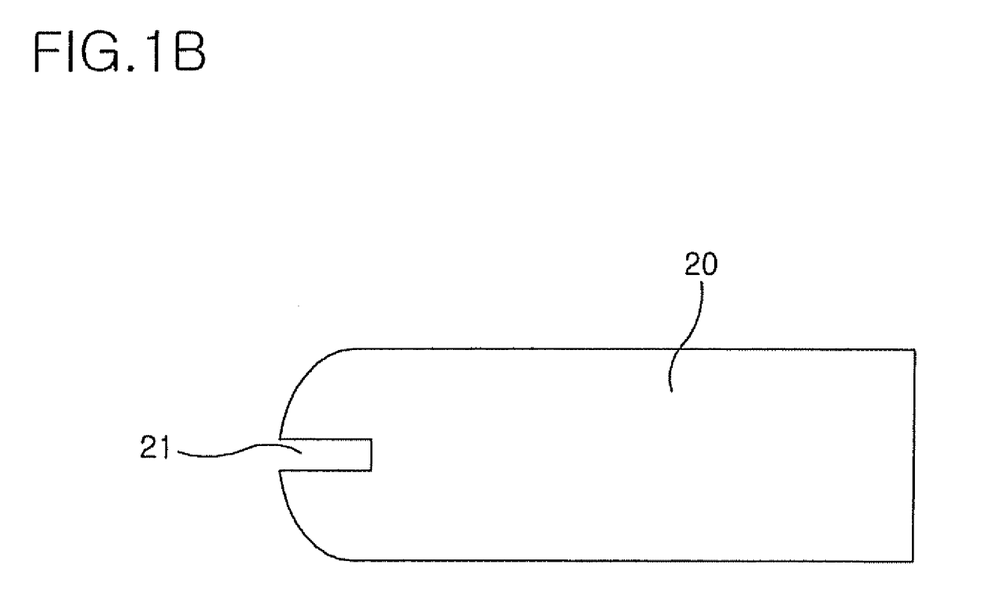
FIG. 1B shows a plan view of an adhesive layer of a biosensor according to an exemplary embodiment of the present invention.

FIG. 1B shows a plan view of an adhesive layer of a biosensor according to an exemplary embodiment of the present invention.

The upper substrate 10 and lower substrate 30 are attached to each other with an adhesive layer 20, such that a capillary is formed by a sample feed 21. The adhesive layer 20 may be a double coated tape with a thickness of 10 to 300 μm. The adhesive layer 20 preferably has a thickness of 10 to 150 μm such that a least amount of the sample is injected. The sample is automatically injected through the sample feed 21 by capillary action, and air existing in the sample feed 21 is discharged through the air outlet 11 of the upper substrate 10.

Figure 1C:
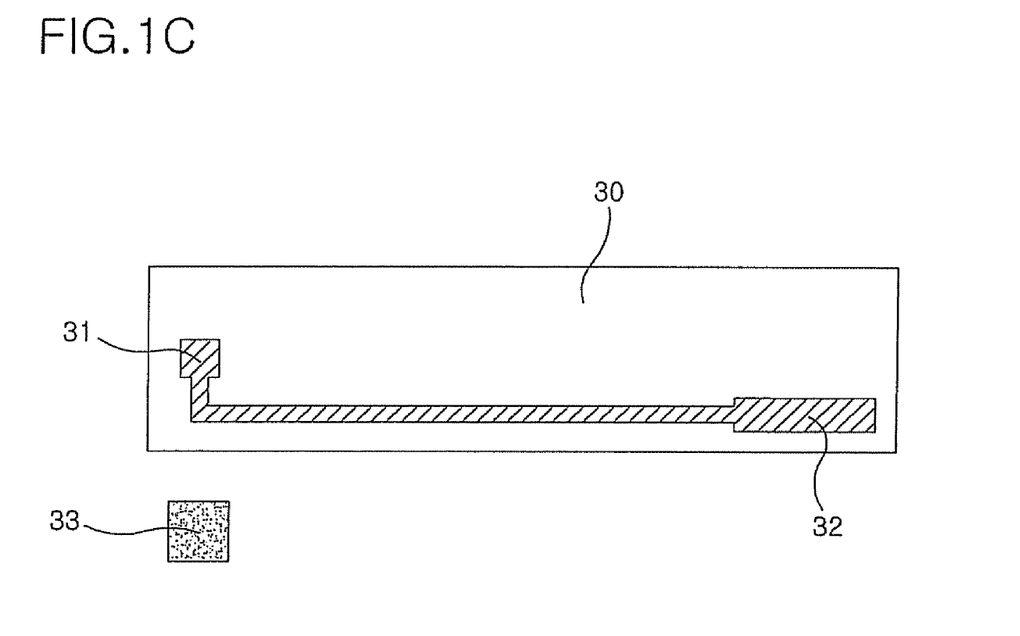
FIG. 1C shows a plan view of a lower substrate of a biosensor according to an exemplary embodiment of the present invention.

FIG. 1C shows a plan view of a lower substrate of a biosensor according to an exemplary embodiment of the present invention.

A lower substrate 30 may be a thin plate made of insulating material, such as polyethylene terephthalate (PET), polyvinyl chloride (PVC) or polycarbonate. The lower substrate 30 may be made of insulating material with a thickness of 50 to 400 μm and, more preferably, with a thickness of 100 to 300 μm.

At least one electrode and at least one connection line are formed on the lower substrate 20. Referring to FIG. 1C, a working electrode 31 and a working electrode connection line 32 are formed on the lower substrate 20. The connection line 32 may be made of the same material as the working electrode 31 or another material such as a conductive material. The lower substrate 30 includes an enzyme reaction layer 33 to measure an analyte contained in a sample. The enzyme reaction layer 33 includes an enzyme, an electron-transfer mediator reacting with the enzyme, and a polymeric scaffold for fixing a buffer solution, an enzyme stabilizer, and other substances to the working electrode or lower substrate 30. The enzyme reaction layer 33 is applied on the working electrode 31 to cover the working electrode 31.

Figure 2:
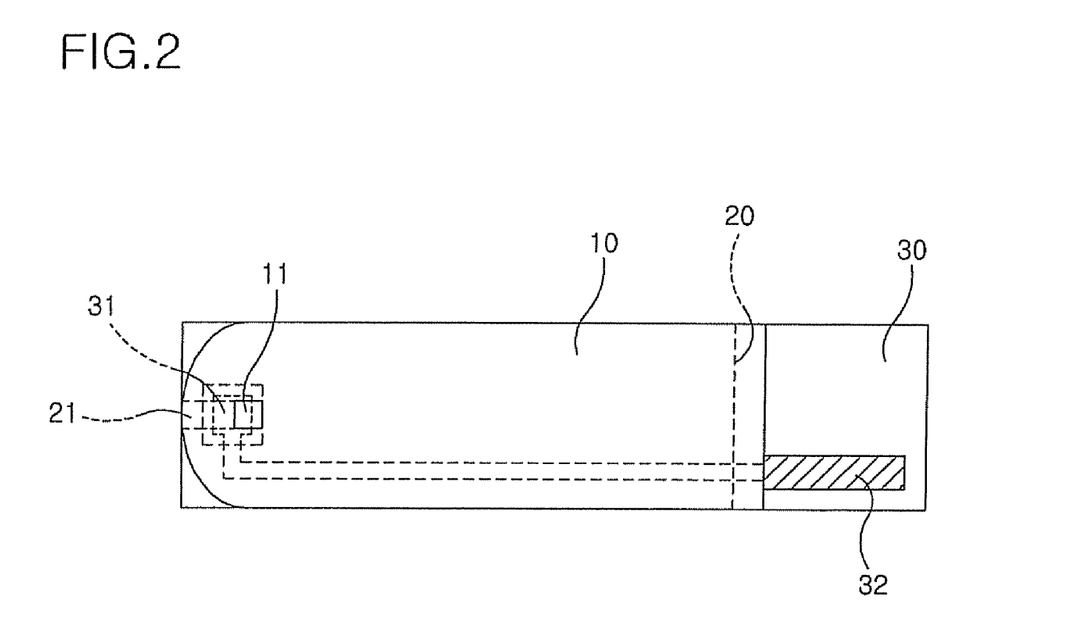
FIG. 2 shows a plan view of a biosensor according to an exemplary embodiment of the present invention.
Figure 3:
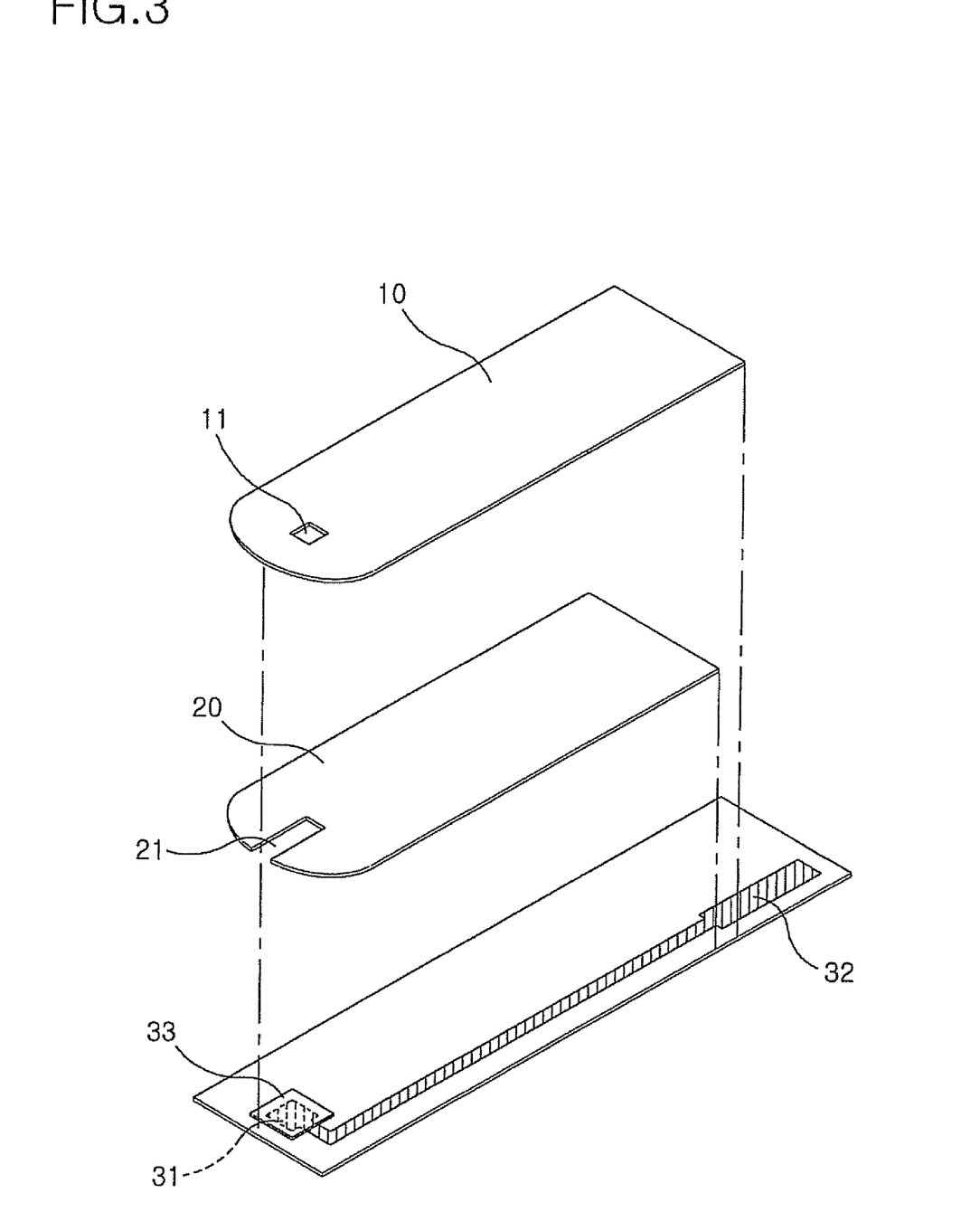
FIG. 3 shows an exploded perspective view of a biosensor according to an exemplary embodiment of the present invention.

FIG. 2 shows a plan view of a biosensor according to an exemplary embodiment of the invention. FIG. 3 shows an exploded perspective view of a biosensor according to an exemplary embodiment of the invention.

For example, when blood is injected through the sample feed 21, blood glucose contained in the blood is oxidized by a glucose oxidase contained in the enzyme reaction layer 33 and the glucose oxidase is reduced. The electron-transfer mediator contained in the enzyme reaction layer 33 is reduced while oxidizing the glucose oxidase. The reduced electron-transfer mediator is electrochemically oxidized again by losing electrons on a surface of the working electrode 31 on which a predetermined voltage is applied. Since the concentration of blood glucose in the blood sample is proportional to current generated when the electron-transfer mediator is oxidized, the concentration of blood glucose can be measured by measuring the amount of the current through the connection line 32. At this time, a left end of the upper substrate acts as a reference or counter electrode, while its right end acts as an electrical contact part connected to a measurement unit.

Figure 4:
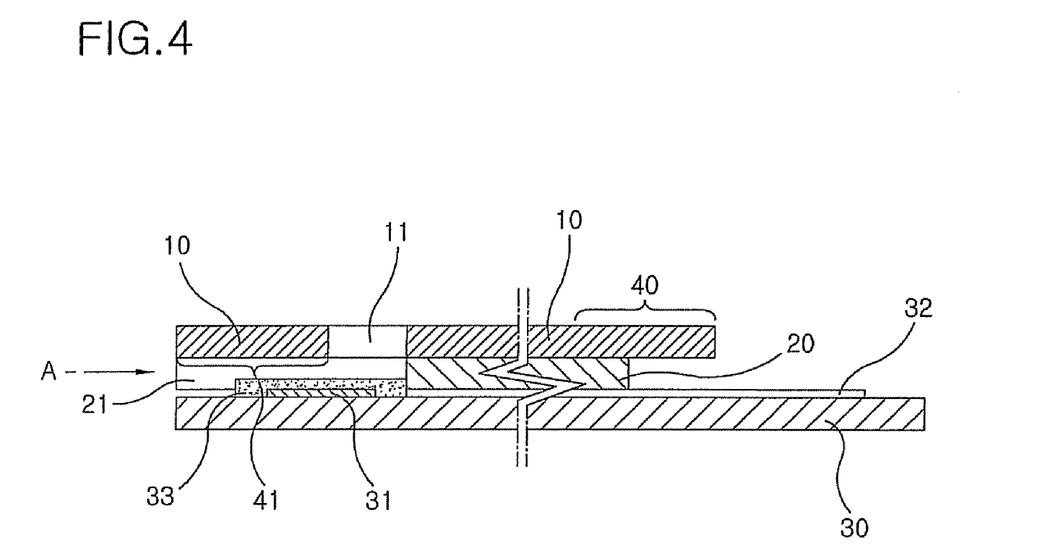
FIG. 4 shows a cross-sectional view of a biosensor according to an exemplary embodiment of the present invention.
Figure 5:
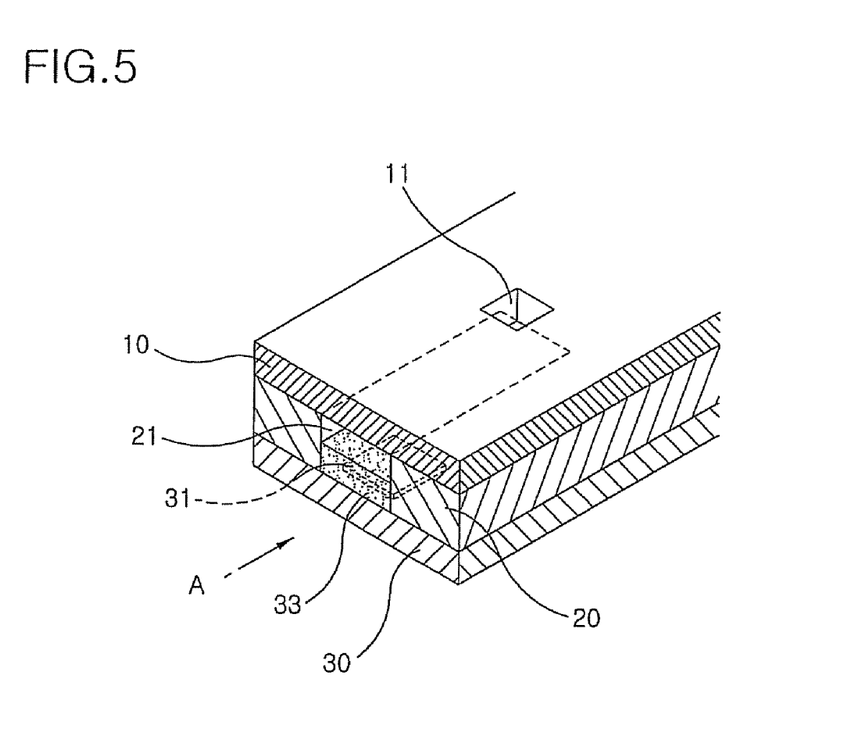
FIG. 5 shows a cross-sectional view of a biosensor as seen from 'A' direction in FIG. 4.

FIG. 4 shows a cross-sectional view of a biosensor according to an exemplary embodiment of the invention. FIG. 5 shows a cross-sectional view of a biosensor as viewed from 'A' shown in FIG. 4.

The working electrode 31 and the working electrode connection line 32 are formed on the insulative lower substrate 30, and the enzyme reaction layer 33 is fixed on the working electrode 31. The lower substrate 30 is coupled with the upper substrate 10 by the adhesive layer 20 having the sample feed 21. The air outlet 11 is formed on the upper substrate 10 made of conductive material to discharge air when a sample is injected through the sample feed 21. The upper substrate 10 preferably has a line resistance of less than 3 kΩ/mm. At this time, an end of the upper substrate 10 acts as an electrode for oxidation or reduction, while the other end acts as an electrical contact part. Accordingly, when the enzyme of the enzyme reaction layer 33 reacts with an analyte, i.e., blood glucose, contained in the sample, oxidation or reduction current that is proportional to the concentration of blood glucose is generated between the working electrode 31 of the lower substrate 30 and the one end of the upper substrate 10, i.e., electrode 41. Accordingly, the concentration of blood glucose can be measured by measuring the oxidation or reduction current by a measurement unit connected to the electrical contact part 40.

Figure 6A:
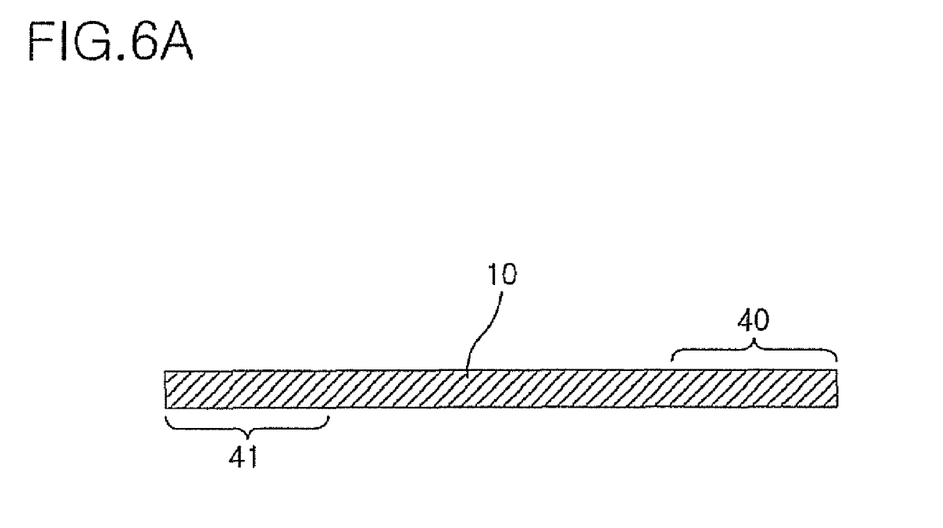
FIGS. 6A and 6B show cross-sectional views of upper substrates of biosensors according to exemplary embodiments of the present invention.
Figure 6B:
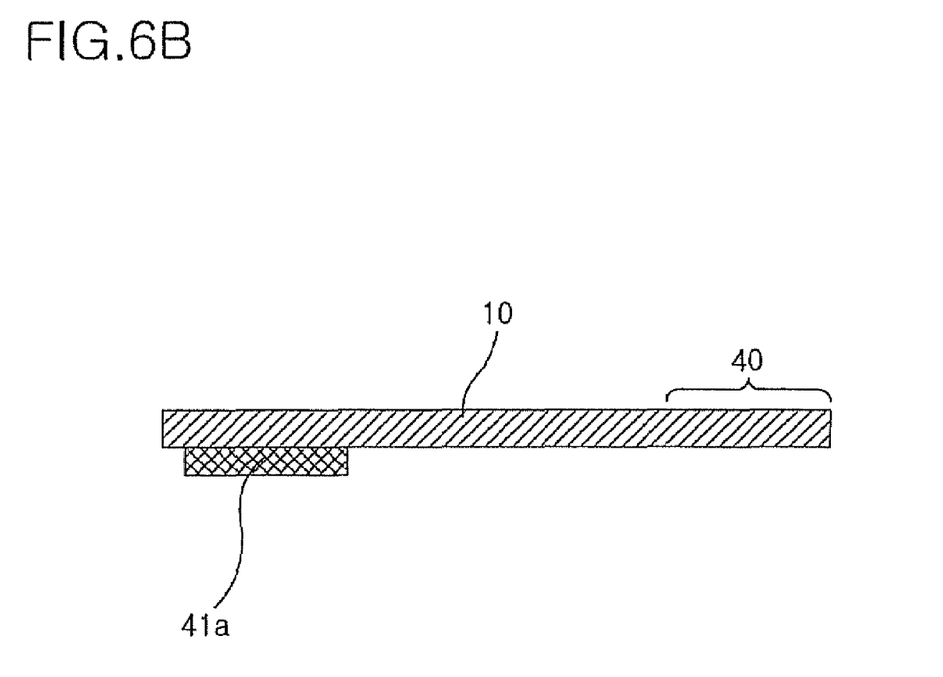

The upper substrate may be provided in various shapes. FIGS. 6A and 6B show cross-sectional views of an upper substrate of a biosensor according to exemplary embodiments of the invention.

Referring to FIG. 6A, a lower part of the upper substrate 10 acts as a reference and/or counter electrode 41 to measure the oxidation or reduction current of the electron-transfer mediator generated by reacting with the analyte contained in the sample, while an upper part on its opposite side acts as an electrical contact part 40 electrically connected to a measurement unit (not shown).

Referring to FIG. 6B, an additional electrode 41a is formed by printing or depositing a material different from that of the upper substrate on the one end of the upper substrate 10 made of a conductive material. The electrode 41a may be used as a reference, counter or working electrode. The material that makes up the electrode 41a may be the same as that of the working electrode 31 formed on the lower substrate 30. Examples of the material include carbon, platinum-plated carbon, silver, silver chloride, palladium, and gold. The electrode 40 or 41a is defined by the sample feed 21 formed on the adhesive layer 20 that fixes the upper and lower substrates to each other.

Figure 7A:
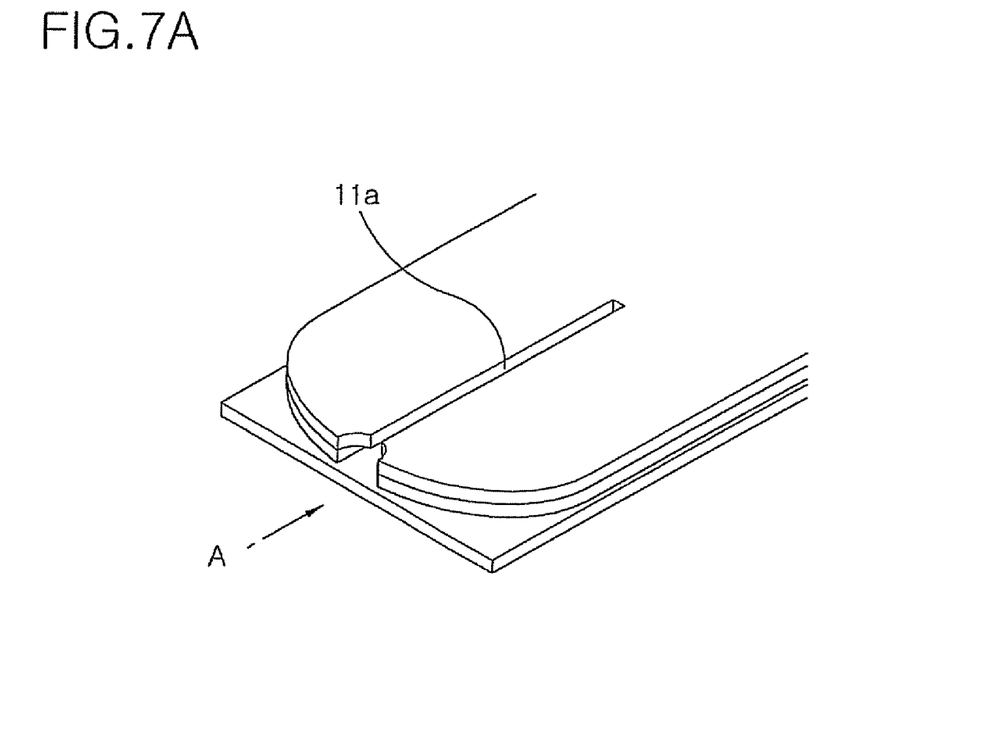
FIGS. 7A and 7B show perspective views of biosensors with upper substrates according to exemplary embodiments of the present invention.
Figure 7B:
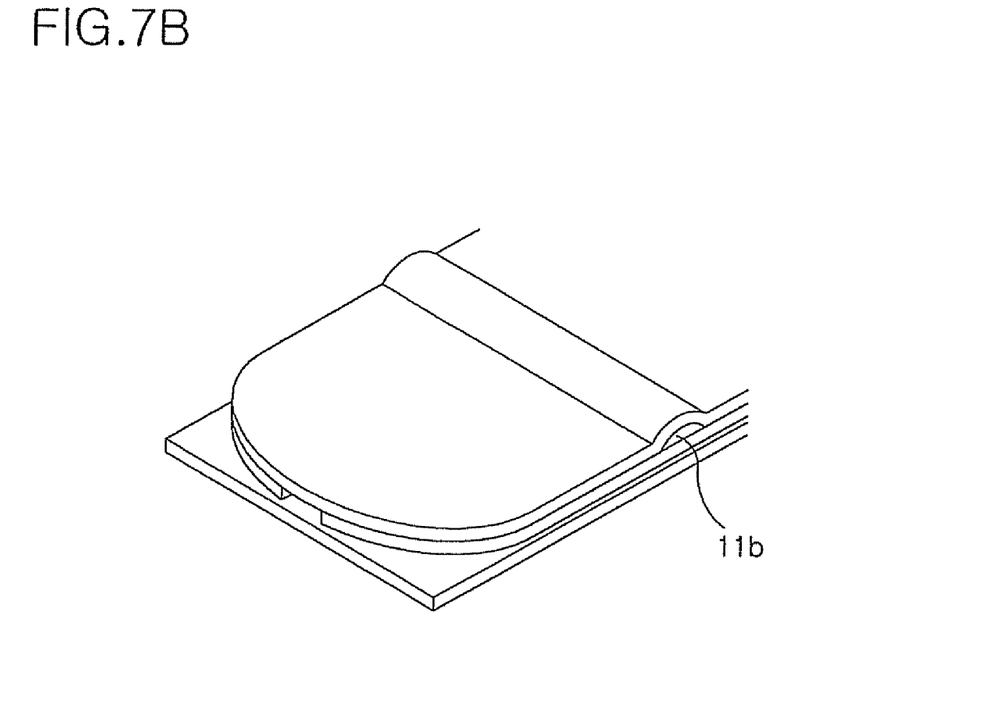

FIG. 7 shows a perspective view of a biosensor having different upper substrates according to an exemplary embodiment of the invention.

FIG. 7A shows an air outlet 11a of an upper substrate that is shaped in a slit shape. FIG. 7B shows an air outlet 11b of an upper substrate that has a protruded shape. The air outlet may be shaped differently from the above.

Figure 8:
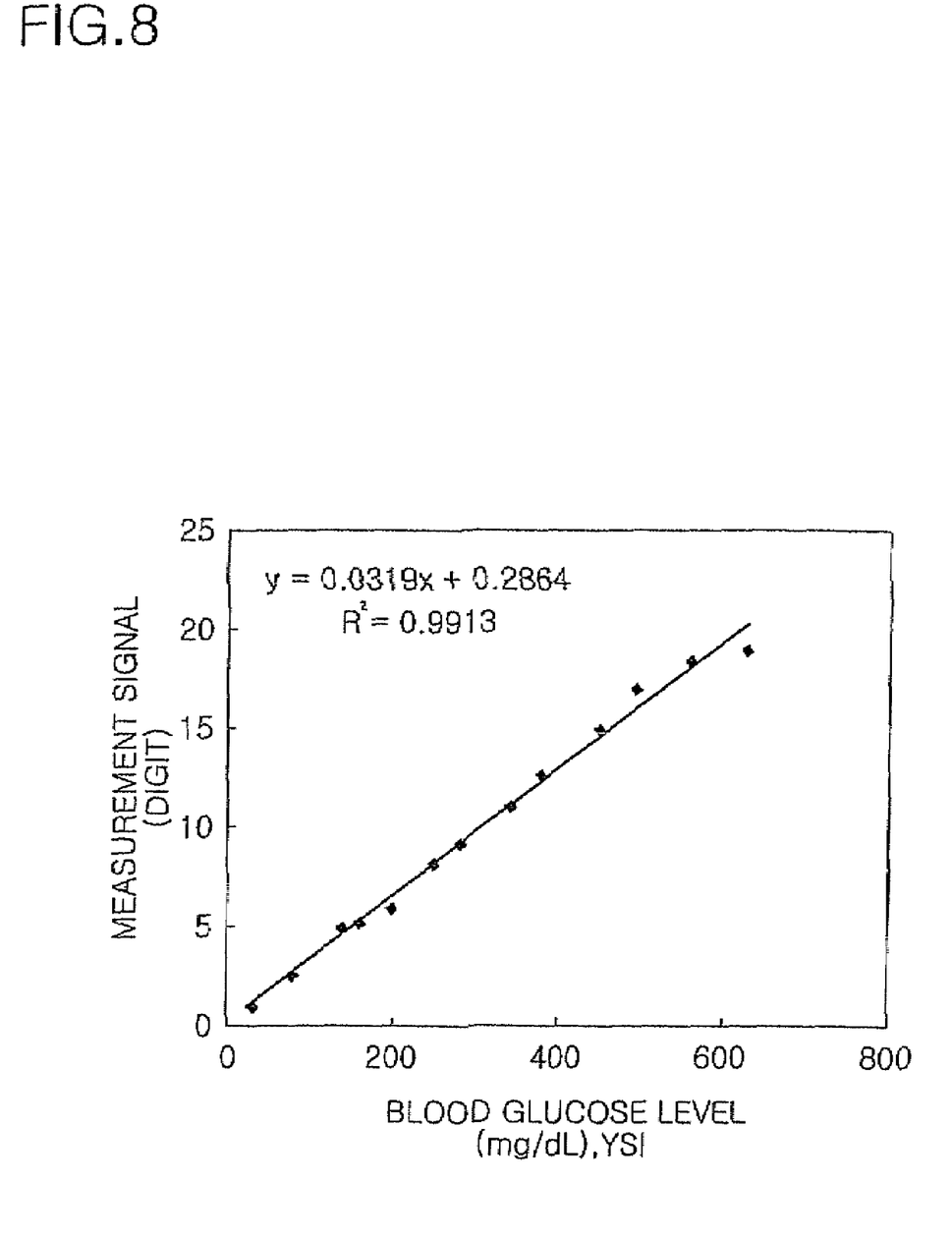
FIG. 8 shows a graph of a correlation between the concentration of blood glucose and a signal when the blood glucose is measured using a biosensor according to an exemplary embodiment of the present invention.

FIG. 8 shows a graph of a correlation between the concentration of blood glucose and a signal when the blood glucose is measured using a biosensor according to an exemplary embodiment of the invention.

In the present embodiment, the upper substrate 10 is formed of an aluminum plate with a thickness of 0.2 mm, and the lower substrate 30 is formed by having the working electrode 31 printed with a carbon/graphite ink (manufactured by Ercon, Inc.) on a PET plate with a thickness of 0.17 mm. The adhesive layer 20 is made by applying an adhesive with a thickness of 0.01 mm on both sides of a transparent PET with a thickness of 0.03 mm. The enzyme reaction layer 33 is formed by dissolving 0.5% carboxylmethylcellulose (CMC) in a phosphate buffer solution of pH7.3. Potassium ferricyanide (K3Fe(CN)6) of 100 mM, an electron-transfer mediator, is dissolved in the resultant solution of 100 mL, and glucose dehydrogenase (GDH) of 1000 U/mL is added and dissolved. The adhesive layer is attached to the lower substrate, and the prepared solution of 0.001 mL is injected to the sample feed 21 using a solution dispenser. After drying it in an oven of 35° C. for 30 minutes, the upper substrate is fixed to the adhesive layer. As a result, a biosensor for blood glucose measurement is fabricated.

FIG. 8 shows a graph of a correlation between the concentration of blood glucose and a signal when the blood glucose is measured using a biosensor according to the above-mentioned exemplary embodiment of the invention. The graph shows that the signal is almost proportional to the concentration of blood glucose.

As apparent from the above description, a biosensor is provided which uses a least amount of blood by designing such that a working electrode and a reference or counter electrode face each other, and is manufactured by a simplified manufacture process by using as an upper substrate an electrode material of the biosensor electrochemically detecting an analyte contained in a sample. Accordingly, it is possible to fabricate the biosensor at lower production cost.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A biosensor measuring an analyte contained in a sample, comprising:
   an insulative lower substrate that has at least one electrode on which an enzyme reaction layer reacting with the analyte is formed;
   an upper substrate that faces the lower substrate and consists of a conductive plate made of a conductive material, the upper substrate having an air outlet; and
   an adhesive layer that has a sample feed with a predetermined height on the enzyme reaction layer and attaches the upper and lower substrate to each other,
   wherein the sample is introduced to the enzyme reaction layer due to capillary phenomenon, an end of the upper substrate acts as a reference electrode in which an electron-transfer mediator contained in the enzyme reaction layer is oxidized or reduced, and the other end acts as an electrical contact part that electrically contacts a measurement unit.

2. The biosensor of claim 1, wherein the one end of the upper substrate acting as an electrode faces the electrode formed on the lower substrate.

3. The biosensor of claim 1, wherein the enzyme reaction layer comprises at least one kind of enzyme and at least one kind of electron-transfer mediator.

4. The biosensor of claim 3, wherein the enzyme is an oxidoreductase, dehydrogenase, transferase, or hydrolase.

5. The biosensor of claim 1, wherein the upper substrate has a line resistance of less than 3 kΩ/mm.

6. The biosensor of claim 1, wherein the electrode formed on the lower substrate is composed of carbon, graphite, platinum-carbon, silver, gold, palladium, or platinum.

7. A biosensor measuring an analyte contained in a sample, comprising:
   an insulative lower substrate that has at least one electrode on which an enzyme reaction layer reacting with the analyte is formed;
   an upper substrate that faces the lower substrate and consists of a conductive plate made of a conductive material, the upper substrate having an air outlet; and
   an adhesive layer that has a sample feed with a predetermined height on the enzyme reaction layer and attaches the upper and lower substrates to each other;
   wherein the sample is introduced to the enzyme reaction layer by virtue of capillary phenomenon, a reference electrode is formed on a lower side of an end of the upper substrate in which an electron-transfer mediator contained in the enzyme reaction layer is oxidized or reduced, and the other end acts as an electrical contact part that electrically contacts a measurement unit.

8. The biosensor of claim 7, wherein the electrode formed on the lower side of the one end of the upper substrate faces the electrode formed on the lower substrate.

9. The biosensor of claim 7, wherein the enzyme reaction layer comprises at least one kind of enzyme and at least one kind of electron-transfer mediator.

10. The biosensor of claim 9, wherein the enzyme is an oxidoreductase, dehydrogenase, transferase, or hydrolase.

11. The biosensor of claim 7, wherein the upper substrate has a line resistance of less than 3 k$\Omega$/mm.

12. The biosensor of claim 7, wherein the electrodes formed on the lower and upper substrates are composed of carbon, graphite, platinum-carbon, silver, gold, palladium, or platinum.

* * * * *